Figure 1:
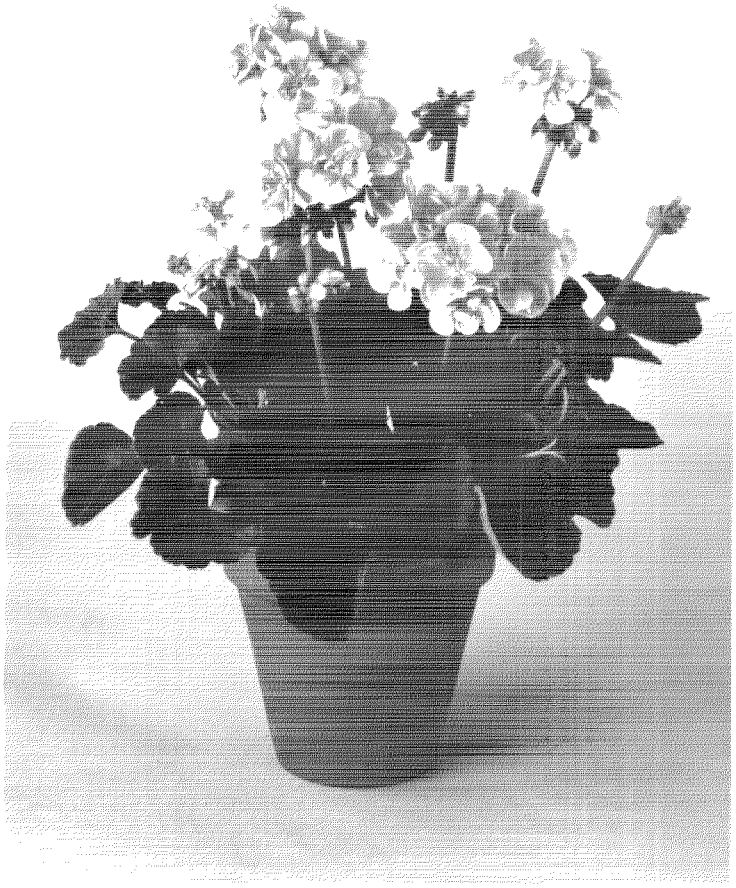
Figure 2:
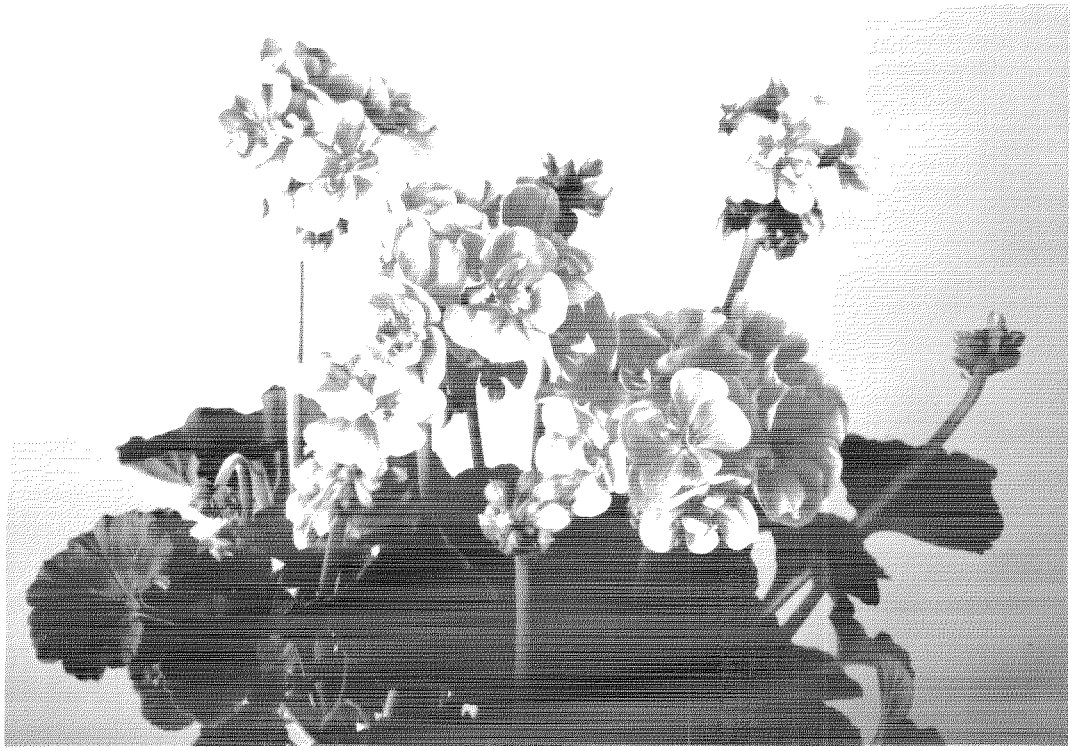
Figure 3:
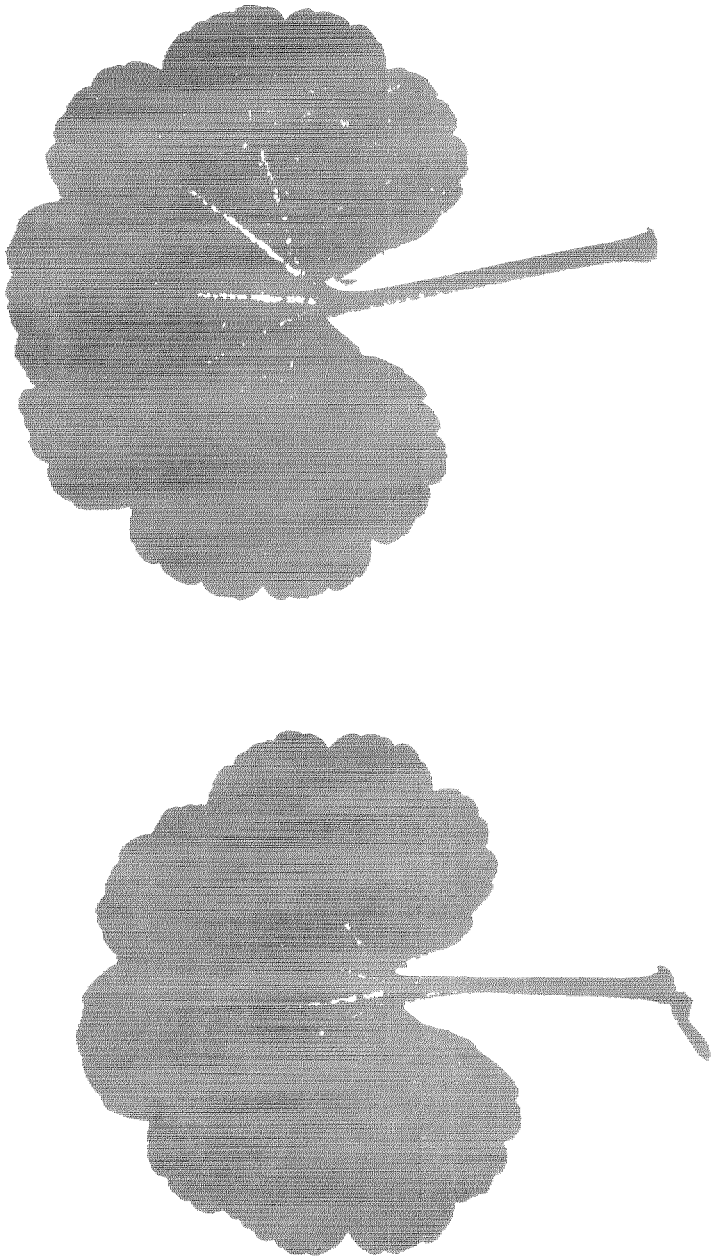

United States Patent [19]

Schumann

[11] Patent Number: Plant 5,368

[45] Date of Patent: Dec. 18, 1984

[54] GERANIUM PLANT NAMED FLEDERMAUS

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 547,883

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of geranium plant names Fledermaus, particularly characterized by the combined features of orange-rose flower color, small leaves and relatively small plant size, very fast rooting, excellent branching, and early flowering.

3 Drawing Figures

1

The present invention comprises a new and distinct cultivar of geranium, botanically known as *Pelargonium zonale,* and hereinafter referred to by the cultivar name Fledermaus.

Fledermaus is a product of planned breeding program which had the objective of creating new geranium cultivars with salmon flower color, semi-double flower form, short plant height, fast rooting, good branching, durable flowers, good zonation, and good chlorophyll quality for transportation.

Fledermaus was originated from a hybridization made in a controlled breeding program in Hillscheid, Federal Republic of Germany in 1979. The female parent was the unpatented cultivar Hillscheider Erfolg, characterized by its salmon semi-double flowers, good zonation, but inferior flower quality. The male parent of Fledermaus was the unpatented cultivar PAC ® Lachsball, a cultivar having salmon semi-double flowers, no zonation, compact habit, and a fast rooting habit.

Fledermaus was discovered and selected as one flowering plant within the progeny of the stated cross by Ingeborg Schumann on June 27, 1980 in a controlled environment in Hillscheid, Federal Republic of Germany.

The first act of asexual reproduction of Fledermaus was accomplished when vegetative cuttings were taken from the initial selection in January, 1981 in a controlled environment in Hillscheid, Federal Republic of Germany by a technician working under formulations established and supervised by Ingeborg Schumann. Horticultural examination of selected units initiated in the Spring of 1981 and continued in 1982 has demonstrated that the combination of characteristics as herein disclosed for Fledermaus are firmly fixed and are retained through successive generations of asexual reproduction.

Fledermaus has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fledermaus which in combination distinguish this geranium as a new and distinct cultivar.

1. Orange-rose flower color.

2

2. Small leaves and relatively small plant size, thereby permitting economic production.
3. Very fast rooting.
4. Excellent branching, producing an average of 4.5 branches per plant.
5. Dark green foliage color.
6. No growth treatment necessary.
7. Early flowering.

Of the many commercial cultivars known to the present inventor, the most similar in comparison to Fledermaus is the female parent Hillscheider Erfolg. Reference is made to attached Chart A which compares certain characteristics of Fledermaus to those same characteristics of Hillscheider Erfolg. In general comparison to Hillscheider Erfolg, Fledermaus has superior branching, smaller leaves and plant size, faster rooting, superior flower production, and a much earlier response.

The accompanying photographic drawings show typical flower and foliage characteristics of Fledermaus with colors being as true as possible with illustrations of this type. Sheet 1 is a color photograph of a potted plant of Fledermaus. Sheet 2 is a relatively enlarged view of the flowers, buds and foliage, and sheet 3 is a black and white print of the underside of the foliage.

In the following description color references are made to The Royal Horticultural Society Colour Chart. In certain instances, color values have alternatively or additionally been given from The Horticultural Colour Chart (H.C.C.). The color values were determined between 2:10 and 2:25 P.M. on Aug. 12, 1983 under 20,000 Klux at Hillscheid, Federal Republic of Germany.

CLASSIFICATION

Botanical: A hybrid of the genus *Pelargonium l'hert.*
Commercial: Fledermaus.

INFLORESCENCE

Umbel:

*Average diameter.*—101 mm.
*Average depth.*—73 mm.
*Peduncle length.*—215 mm.
*Pedicel length.*—20 mm. (⅔ strength anthocyan at an open corolla)

Corolla:

*Average diameter.*—45 mm.
*Form.*—Semi-double, nearly rotate.

*Color (general tonality from a distance of three meters).*—R.H.S. 41C, H.C.C. 619.

*Color (abaxial).*—H.C.C. 619, R.H.S. 41D.

*Color (adaxial).*—H.C.C. 621-621/3.

Bud:

*Shape.*—Elliptic to narrow elliptic.

*Color (abaxial).*—Nearly white.

Reproductive organs:

*Androecium.*—Monodelphous; 6-7 stamens; plentiful pollen.

*Gynoecium.*—4-5 Lobed stigma, color red; style color red.

Spring flowering response period: In Hillscheid, Federal Republic of Germany, 70% of plants with at least 1 flower opened 13 weeks after planting of unrooted cuttings.

Outdoor flower production: In the flower count in 1982 in Hillscheid, Federal Republic of Germany, between 69 and 73 flowers per plant were noted for the June through Oct. observation period.

Durability: Shatter resistance good.

PLANT

Foliage:

*Form.*—Kidney-shaped.

*Margin.*—Bicrenate.

*Color (abaxial).*—Medium to dark green.

*Color (zonation).*—Dark brown.

*Tolerance to botrytis.*—Good.

General appearance and form:

*Internode length.*—33 mm.

*Branching pattern.*—Excellent, with an average of 4.5 branches per plant being produced.

*Height.13* 230 mm.; small.

CHART A

| | Hillscheider Erfolg | Fledermaus |
|---|---|---|
| Branching Habit (number of branches of non-pinched plants 13 weeks after planting unrooted cutting) | 3.3 | 4.5 |
| Hillscheid Spring Flowering Response | 0% | 70% (very early) |
| Zonation | very strong | strong |
| Foliage Form | round | kidney shaped |
| Leaf Base | closed | open |
| Plant height | medium | small |
| Outdoor Flower Production | 51-54 | 69-73 |

I claim:

1. A new and distinct cultivar of geranium plant named Fledermaus, as described and illustrated, and particularly characterized by the combined features of orange-rose flower color, small leaves and relatively small plant size, very fast rooting, excellent branching, and early flowering.

* * * * *